US011259473B2

(12) United States Patent
Liu et al.

(10) Patent No.: US 11,259,473 B2
(45) Date of Patent: Mar. 1, 2022

(54) TMV RESISTANT TOBACCO PLANT CONTAINING SHORT N INTRODUCED FRAGMENT AND METHOD FOR BREEDING SAME

(71) Applicant: Yunnan Academy of Tobacco Agricultural Sciences, Yunnan (CN)

(72) Inventors: Yong Liu, Yunnan (CN); Changjun Huang, Yunnan (CN); Yongping Li, Yunnan (CN); Haiqin Yu, Yunnan (CN)

(73) Assignee: YUNNAN ACADEMY OF TOBACCO AGRICULTURAL SCIENCES, Yunnan (CN)

(*) Notice: Subject to any disclaimer, the term of this patent is extended or adjusted under 35 U.S.C. 154(b) by 0 days.

(21) Appl. No.: 16/648,284

(22) PCT Filed: Sep. 20, 2017

(86) PCT No.: PCT/CN2017/102444
§ 371 (c)(1),
(2) Date: Mar. 18, 2020

(87) PCT Pub. No.: WO2019/056206
PCT Pub. Date: Mar. 28, 2019

(65) Prior Publication Data
US 2021/0120752 A1    Apr. 29, 2021

(51) Int. Cl.
*A01H 5/12*    (2018.01)
*A01H 1/04*    (2006.01)
*A01H 1/00*    (2006.01)
*A01H 6/82*    (2018.01)

(52) U.S. Cl.
CPC ............ *A01H 1/126* (2021.01); *A01H 1/045* (2021.01); *A01H 5/12* (2013.01); *A01H 6/823* (2018.05)

(58) Field of Classification Search
CPC ........ A01H 1/126; A01H 6/823; A01H 1/045; A01H 5/12
See application file for complete search history.

(56) References Cited

U.S. PATENT DOCUMENTS

| 4,520,020 A | 5/1985 | Loebenstein et al. |
| 6,372,962 B1 | 4/2002 | Baker et al. |

FOREIGN PATENT DOCUMENTS

| CN | 1157549 A | 8/1997 |
| CN | 101892304 A | 11/2010 |
| CN | 103866038 B | 9/2015 |
| CN | 105200052 A | 12/2015 |
| CN | 105200149 A | 12/2015 |
| CN | 105274120 B | 7/2018 |
| CN | 104830982 B | 8/2018 |

OTHER PUBLICATIONS

Bagley, C. A. (2001). Controlling tobacco mosaic virus in tobacco through resistance (Doctoral dissertation, Virginia Tech (Year: 2001).*
Lewis, R. S., S. R. Milla, and J. S. Levin. "Molecular and genetic characterization of *Nicotiana glutinosa* L. chromosome segments in tobacco mosaic virus-resistant tobacco accessions." Crop science 45.6 (2005): 2355-2362. (Year: 2005).*
Leitch, I. J., et al. "The ups and downs of genome size evolution in polyploid species of *Nicotiana (Solanaceae)*." Annals of botany 101.6 (2008): 805-814. (Year: 2008).*
Sierro, Nicolas, et al. "The tobacco genome sequence and its comparison with those of tomato and potato." Nature communications 5.1 (2014): 1-9. (Year: 2014).*
Lewis, Ramsey S., and Cara Rose. "Agronomic Performance of Tobacco Mosaic Virus-Resistant Tobacco Lines and Hybrids Possessing the Resistance Gene N Introgressed on Different Chromosomes." Crop science 50.4 (2010): 1339-1347. (Year: 2010).*
International Search Report/Written Opinion in related/corresponding PCT Application No. PCT/CN2017/102444 dated Jun. 8, 2018.
R.S. Lewis et al., "Molecular and Genetic Characterization of *Nicotiana glutinosa* L. Chromosome Segments in Tobacco Mosaic Virus-Resistant Tobacco Accessions," Crop Science, Nov. 2005, pp. 2355-2362, vol. 45.
Yong Liu et al., "N Introgression Segment Length Polymorphism of Newly Tested *Nicotiana Tabacum* Germplasm Highly Resistant to Tobacco Mosaic Virus," Sep. 6, 2017, pp. 95-98, vol. 23, No. 6, including English abstract.

* cited by examiner

*Primary Examiner* — Weihua Fan
(74) *Attorney, Agent, or Firm* — Patent Portfolio Builders PLLC

(57) ABSTRACT

A TMV resistant tobacco plant containing a short N introgressed segment and a method for breeding the same. A homozygous tobacco plant containing an N introgressed segment is hybridized with a tobacco plant of genotype nn to obtain an F1 progeny tobacco plant of genotype Nn. The F1 progeny tobacco plant is hybridized with the tobacco plant of genotype nn, to obtain population materials for screening to obtain the short N introgressed segment. TMV is inoculated at a seedling stage, and Nn genotype plants showing necrotic lesion are obtained by screening the population materials. The Nn genotype plants are genotyped using a molecular marker TN5.51 primer pair and an N gene-specific molecular marker N1N2 at the right end of the N introgressed segment. A plant found to be negative when tested by the TN5.51 primer pair and to be positive when tested by the N1N2 molecular marker is a plant comprising the short N introgressed segment. The size of non-target genomic components deleted from plants containing the short N introgressed segment is estimated using TN5.34 and TN5.20 and TN4.99 primer pairs. The obtained short N introgressed segment is applicable to germplasma innovation and breeding of TMV resistant tobacco. The invention is helps to reduce linkage drag with the N gene.

8 Claims, 1 Drawing Sheet
Specification includes a Sequence Listing.

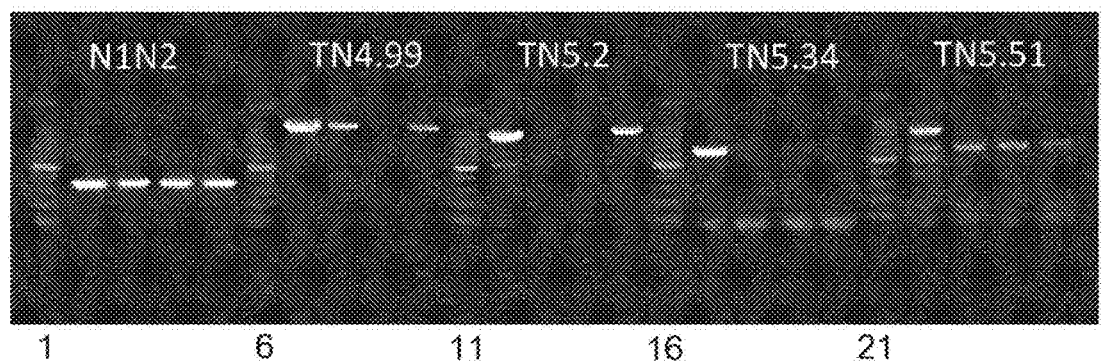

TMV RESISTANT TOBACCO PLANT CONTAINING SHORT N INTRODUCED FRAGMENT AND METHOD FOR BREEDING SAME

FIELD OF THE INVENTION

The invention relates to the field of tobacco breeding, particularly to a TMV-resistant tobacco plant comprising a short N introgressed segment and a method for breeding the same.

BACKGROUND OF THE INVENTION

Tobacco mosaic virus (TMV) is a major disease on tobacco (*Nicotiana tabacum* L.). Plantation of a TMV-resistant variety is still the most fundamental and most cost-effective means of preventing and controlling TMV. A resistant variety to be promoted need to be a variety with high resistance, and without negative influence in terms of yield and agronomic traits.

Currently, TMV resistance for cultivar tobacco is mainly derived from a wild tobacco species of *Nicotiana glutionsa*, and the resistance thereof is controlled by one dominant single gene (N). The N gene was cloned in 1994 and is the first NBSs resistant gene cloned in plants. N gene is resistant to TMV-U1 line. The genomic sequence size of the N gene is 6656 bp, including 5 exons and 4 introns, belonging to resistant gene of TIR-NBS-LRR type. The resistant mechanism of N gene is to trigger hypersensitive necrotic spots (lesions) at the site of virus infection, and the movement of TMV in the plant is restricted by inducing hypersensitive cell death. After mediating the hypersensitivity reaction, tobacco plants can acquire systemic resistance, which produces a broad-spectrum resistance to re-invasion of TMV or other similar pathogens. Through a series of conventional hybridization and backcrossing, the resistance of N gene is transferred from *Nicotiana glutionsa* to an oriental tobacco and then to a tobacco variety. Transferring the resistance of N gene by hybridization is actually transferring a chromosome segment of *Nicotiana glutionsa* comprising N gene (abbreviated as N introgressed segment). N introgressed segment is used for almost all TMV-resistant tobacco breeding in the world. A representative variety is TMV resistant tobacco varieties comprising N introgressed segment planted commercially earlier, i.e. Coker176 and Speight H20. Due to linkage drags involving such as low yield and slow yellowing of the upper leaves, the tobacco varieties comprising an N introgressed segment as long as that of Coker176 could not meet the urgent needs of production. It has been proved that N gene itself do not involve any linkage drag of yield and output, and such a linkage drag is derived from the non-target genomic component (abbreviated as drag genomic component) linked to N gene on the N introgressed segment as long as that of Coker176. It is expected to reduce the linkage drag of the N introgressed segment by reducing the non-target genomic component linked to N gene on the N introgressed segment as long as N introgressed segment of Coker176. However, the N introgressed segment has low homology with the common tobacco chromosome, and thus it is possible but quiet low frequency for chromosome crossover between the N introgressed segment and the common tobacco (with a probability of about 1/2000). Even if any chromosome crossover occurs, a chromosome-crossovered plant with a short N introgressed segment (Ns segment) cannot be screened out from the breeding population by conventional breeding techniques. Because the drag phenotype as a quantitative trait is susceptible to environmental conditions and is difficult to be screened out in the early stage of breeding. In addition, the lack of technical means for detecting non-target genomic components linked to IV gene on the N introgressed segment hinders the breakthrough in TMV-resistant tobacco breeding. Therefore, how to overcome the negative influence of the prior art is an urgent problem to be solved in the field of TMV-resistant tobacco breeding.

SUMMARY OF THE INVENTION

The present invention is directed to address the negative influence of the prior art and to provide a TMV-resistant tobacco plant comprising a short N introgressed segment and a method for breeding the same. The drag genomic component linked to N gene is deleted from the TMV-resistant tobacco plant comprising the short N introgressed segment. The linkage drag of the N introgressed segment can be therefore reduced. It can be used for breeding a tobacco variety with high TMV resistance and without obvious negative influence in terms of yield and quality. In the context of the present invention, the term "N introgressed segment" refers to a chromosome segment of a wild species tobacco comprising a TMV-resistant gene (N gene).

The term "short N introgressed segment" refers to a DNA segment in which the non-target genomic component (abbreviated as drag genomic component) linked to N gene on the N introgressed segment is partially or completely deleted, and the intact function of the N gene is retained.

The term "drag genomic component" refers to a genomic component comprising a drag gene but not N gene on the N introgressed segment.

The present invention is further directed to provide a method of obtaining a TMV-resistant tobacco plant comprising a short N introgressed segment.

The present invention is further directed to use of a TMV-resistant tobacco plant comprising a short N introgressed segment in breeding a TMV-resistant tobacco variety.

The present invention provides a TMV-resistant tobacco plant comprising a short N introgressed segment, wherein the drag genomic component is reduced by at least 0.51 Mb, preferably at least 0.93 Mb, more preferably at least 1.56 Mb in the short N introgressed segment, compared to that in an N introgressed segment of Coker176 type tobacco accessions.

In one preferred embodiment of the invention, partial or entire sequence of SEQ ID No. 13 is at least deleted in the short N introgressed segment, compared to N introgressed segment of Coker176 type tobacco accessions.

In another preferred embodiment of the present invention, at least a sequence corresponding to bases at positions of 806,912 to 1,404,293 in the sequence of SEQ ID No. 13 is deleted in the short N introgressed segment, as compared to the N introgressed segment of Coker176 type tobacco accessions.

In another preferred embodiment of the present invention, the TMV-resistant tobacco plant is selected from the group consisting of:

a) a tobacco plant that is detected as positive for the N1N2 marker and negative for both of the TN5.34 primer pair and the TN5.51 primer pair;

b) a tobacco plant that is detected as positive for the N1N2 marker and negative for the TN5.20 primer pair, the TN5.34 primer pair and the TN5.51 primer pair; and c) a tobacco plant that is detected as positive for the N1N2 marker and negative for the TN4.99 primer pair, the TN5.20 primer pair, the TN5.34 primer pair and the TN5.51 primer pair.

In another preferred embodiment of the invention, the short N introgressed segment is obtained by means of chromosome crossover, genome editing, chemical mutagenesis or physical mutagenesis.

In still another preferred embodiment of the present invention, the TMV-resistant tobacco plant is derived from Nicotiana genus, preferably from flue-cured tobacco, burley tobacco, oriental tobacco, sun-cured tobacco or cigar tobacco.

The present invention provides a tobacco hybrid, a variety or a line bred with the TMV-resistant tobacco plant comprising a short N introgressed segment.

The present invention provides a seed, a pollen and an ovule of the TMV-resistant tobacco comprising a short N introgressed segment.

The invention also provides use of a TMV-resistant tobacco plant comprising a short N introgressed segment in breeding a TMV-resistant tobacco variety.

The present invention also provides a method of breeding a TMV-resistant tobacco plant comprising a short N introgressed segment comprising a) hybridizing a tobacco plant having a homozygous N introgressed segment with a tobacco plant having nn genotype to obtain a F1 tobacco plant having Nn genotype, and then hybridizing the F1 tobacco plant with the tobacco plant having nn genotype to obtain a population material for screening the short N introgressed segment;

b) inoculating TMV to the population material obtained in step a) during the seedling stage, and screening a Nn genotype plant exhibiting lesions in the population material; and c) genotyping the Nn genotype plant screened in step b) with a molecular marker of TN5.51 primer pair at the right end of the N introgression segment and N gene-specific molecular marker N1N2, and screening a plant detected as positive for the molecular marker N1N2 and negative for the TN5.51 primer pair.

The present invention also provides a method of breeding a TMV-resistant tobacco plant comprising a short N introgressed segment comprising a) hybridizing a tobacco plant having homozygous N introgressed segment with a tobacco plant having nn genotype to obtain a F1 tobacco plant having Nn genotype, and then hybridizing the F1 tobacco plant with a tobacco plant having nn genotype to obtain a population material for screening the short N introgressed segment;

b) inoculating TMV to the population material obtained in step a) during the seedling stage, and screening a plant with Nn genotype exhibiting lesions in the population material; and c) genotyping the Nn genotype plant screened in step b) with TN5.34 primer pair, TN5.51 primer pair and N gene-specific molecular marker N1N2, and screening a plant detected as positive for the molecular marker N1N2 and negative for the TN5.34 primer pair and the TN5.51 primer pair.

The present invention also provides a method of breeding a TMV-resistant tobacco plant comprising a short N introgressed segment comprising a) hybridizing a tobacco plant having homozygous N introgressed segment with a tobacco plant having nn genotype to obtain a F1 tobacco plant having Nn genotype, and then hybridizing the F1 tobacco plant with a tobacco plant having nn genotype to obtain a population material for screening the short N introgressed segment;

b) inoculating TMV to the population material obtained in step a) during the seedling stage, and screening a plant with Nn genotype exhibiting lesions in the population material; and c) genotyping the Nn genotype plant screened in step b) by using TN5.20 primer pair, TN5.34 primer pair, TN5.51 primer pair and N gene-specific molecular marker N1N2, and screening for a plant detected as positive for the molecular marker N1N2 and negative for the TN5.20 primer pair, the TN5.34 primer pair and the TN5.51 primer pair.

The present invention also provides a method of breeding a TMV-resistant tobacco plant comprising a short N introgressed segment comprising a) hybridizing a tobacco plant having homozygous N introgressed segment with a tobacco plant having nn genotype to obtain a F1 tobacco plant having Nn genotype, and then hybridizing the F1 tobacco plant with a tobacco plant having nn genotype to obtain a population material for screening the short N introgressed segment;

b) inoculating TMV to the population material obtained in step a) during the seedling stage, and screening for a plant with Nn genotype exhibiting lesions in the population material; and c) genotyping the Ain genotype plant screened in step b) by using TN4.99 primer pair, TN5.20 primer pair, TN5.34 primer pair, TN5.51 primer pair and N gene-specific molecular marker N1N2, and screening for a plant detected as positive for the molecular marker N1N2 and negative for the TN4.99 primer pair, the TN5.20 primer pair, TN5.34 primer pair and the TN5.51 primer pair.

The present invention provides use of a short N introgressed segment in a. TMV-resistant tobacco plant, wherein the drag genomic component is reduced by at least 0.51 Mb, preferably at least 0.93 Mb, more preferably at least 1.56 Mb in the short N introgressed segment, compared to that in N introgressed segment of Coker176 type tobacco accessions.

In a preferred embodiment of the invention, at least partial or entire of the sequence of SEQ ID No. 13 is deleted in the short N introgressed segment, compared to N introgressed segment of Coker176 type tobacco accessions.

In a preferred embodiment of the invention, the use results in a tobacco plant selected from the group consisting of:

a) a tobacco plant that is detected as positive for the marker N1N2 and negative for both of the TN5.34 primer pair and the TN5.51 primer pair;

b) a tobacco plant that is detected as positive for the marker N1N2 and negative for the TN5.20 primer pair, the TN5.34 primer pair and the TN5.51 primer pair; and c) a tobacco plant that is detected as positive for the marker N1N2 and negative for the TN4.99 primer pair, the TN5.20 primer pair, the TN5.34 primer pair and the TN5.51 primer pair.

In a preferred embodiment of the invention, the short N introgressed segment is obtained by means of chromosome crossover, genome editing, chemical mutagenesis or physical mutagenesis.

In a preferred embodiment of the present invention, the tobacco plant is derived from Nicotiana genus, preferably from flue-cured tobacco, burley tobacco, oriental tobacco, sun-cured tobacco or cigar tobacco.

The present invention also provides a tobacco hybrid, a variety or a line bred from the tobacco plant obtained according to the use described above.

The present invention also provides a seed, a pollen and an ovule of the tobacco plant obtained according to the use described above.

In the context of the present invention, a tobacco having homozygous N introgressed segment refers to a tobacco comprising an N introgressed segment, preferably a common tobacco comprising an N introgressed segment as long as that of Coker176 variety, including, but not limited to flue-cured tobacco, burley tobacco, sun-cured tobacco, oriental tobacco, cigar tobacco, and other tobacco varieties. The N introgressed segment as long as that of Coker176 type is characterized in that it is detected as negative for the GL4.06 primer pair and positive for the TN5.51 primer pair. A common tobacco comprising an N introgressed segment as long as that of Coker176 type includes, but is not limited to 6349, 7402, 7915, 8100, 8211, 8212, 78-3013, 8902-42, B09, Burley21, B22, B49, B64, Banket-A-1, BG4, BYS, CV85, V87, Coker 86, Coker 51, Coker176, EMH14, Ergo, ETWM10, GH12, K10, K14, Ky10, Ky12, Ky 41A, Ky14, Ky15, Ky17, Ky171, Ky56, Ky8959, Ky8959 (BC4), Ky9, Ky907 (BC4), Ky908, MS ky17, MBN2, MS Burley21 X Ky14, MRS-3, MS B21, MS Ky10, MSKy14XL8, NC3, NC567, NC7, NC86, PVH01, PVH02, PVH05, PVH06, PVH07, PVH08, RGH04, SC71, SC72, TN97, Vamoor 48, Virginia 1, Virginia 3160, Virginia 645, Virginia 770, Virginia 80, Va 1048, WE-12, WB68, RT32, Bayin No. 1, Dabaijin 2518, Liaoyan No. 9, Liaoyan No. 14, Mudan 80-7, Mudan 81-56, Taiyan No. 5, Taiyan No. 6, Wutongyan 1012, Zhongwei No. 1, Yinba 1, Yunyan 202402, 521, 911, 8358, Blue star 100, Burley mammoth ky16, Burley21, 06160, CCC-h, CCC-L, Coker 51, Ex 12, Gen 164, Gen 224, Gr 38a, Havana 425, Havana 426, Havana 503b, Havanan 503, Holmes breeding line-1, KHD926, KY165, KY21, KY22, KY35, KY8654, lancaster seed, M-1, Massck-1, MD A30, MD B100, MD40, MD402, Metacomet, MRS-1, MRS-3, NC102, NC297, NC-BMR 90, NIC 112, NIC 112B (PL10), NIC 112b (PL11), NIC 112C-G (PL271), NIC 112C-G (PL37), NIC 117D-1B, OS 802, Poquonock, Southern beauty, Vamorr48, and WB68.

A tobacco with nn genotype refers to a tobacco without N gene, preferably; a common tobacco without N gene, including but not limited to flue-cured tobacco, burley tobacco, sun-cured tobacco, oriental tobacco and cigar tobacco and other common tobacco varieties. The phenotypic trait of tobacco with nn genotype includes disease resistance, high yield, high grade index, easily cured, leaf quality; plant height, a mature characteristic of early to late maturity, and a moderate to large number of plant leaves. The tobacco having nn genotype preferably includes, but is not limited to, K326, Yunyan 87, Yunyan, 97, Yunyan, 85, NC89, Zhongyan 100, Honghuadajinyuan, and Cuibi No. 1.

The tobacco hybrid, variety or line consists of a plant comprising short N introgressed segment. The plant comprising the short N introgressed segment was TMV-resistant and reduced in the non-target genomic component linked to N gene, compared with the plant comprising the N introgressed segment. At least partial or entire sequence in SEQ ID No. 13 is deleted from the plant comprising the short N introgressed segment. The plant comprising the short N introgressed segment is detected as negative for both of the GL4.06 primer pair and the TN5.51 primer pair. Preferably, the plant is detected as negative for the TN4.99 primer pair or the TN5.30 primer pair or the TN5.34 primer pair.

A method to obtain a plant comprising a short N introgressed segment in which at least partial or entire sequence of SEQ ID No, 13 is deleted, comprises obtaining a Nn population material by means of hybridization breeding, and screening a plant with chromosome crossover. Genome editing method, chemical mutagenesis, physical mutagenesis or biotechnology can also be used. The chemical or physical mutagenesis method is used to screen a mutant in which partial to entire sequence of SEQ ID No. 13 is deleted. The chemical mutagenesis method includes treatment with a mutagenesis agent such as sodium azide, ethidium bromide, and ethyl methanesulfonate. The physical mutagenesis method includes X-rays, gamma rays, fast neutron radiation, heavy ion radiation, and ultraviolet radiation. The genome editing method of biotechnology includes knocking out partial to entire sequence of SEQ ID No. 13 by using CRISPR/Cas9 technology, zinc finger endonuclease (ZFN) technology, and transcription-activator-like effector nuclease (TALEN) technology. The partial sequence has an appropriate length that is not particularly limited, for example, 1 bp, 10 bp, 100 bp, 1 Kb, 10 Kb, 100 Kb, or 1000 Kb in length, or 2000 Kb in full length.

Process of screening for TMV-resistant tobacco plant comprising the short N introgressed segment by using hybridization and molecular marker screening techniques comprises hybridizing a tobacco plant comprising homozygous N introgressed segment and negative for the GL4.06 primer pair and positive for the TN5.51 primer pair, with the tobacco plant having nn genotype, to obtain the descendant plant with Nn genotype. The Nn descendant plant was hybridized with the tobacco plant having the nn genotype, to obtain a population material used for screening the short N introgressed segment. TMV is inoculated at a seedling stage, and Nn genotype plant showing lesions are obtained by screening from the population material. The Nn genotype plant is extracted for DNA and genotyped with the molecular marker TN5.51 primer pair at the right end of the N introgressed segment and the N gene-specific molecular marker N1N2. The plant detected as negative for the TN5.51 primer pair and positive for the N1N2 molecular marker is screened out, which is the plant containing the short N introgressed segment.

The Nn descendant is hybridized a tobacco having the nn genotype, to obtain the population material used for screening the short N introgressed segment. The population material includes a breeding population material comprising the Nn genotype. Backcrossing population material of BC1F1, BC2F1, BC3F1, BC4F1, BCSF1 . . . , and BCnF1 materials are preferred, with n representing the number of generations of backcrossing and can be 6, 7, 8, 9, 10, 15, and 20. Other population materials are also included, such as self-crossing population material F2 comprising the Nn genotype.

A method for screening Nn genotype plant from the breeding population material comprising Nn genotype includes artificial inoculation of TMV, and also molecular marker-assisted screening method depending on resistant phenotypes. A preferred method for screening resistant phenotype includes: inoculating TMV during seedling stage, and screening out the plant exhibiting lesions used for screening the plant comprising the short N introgressed segment from the population material. A molecular marker-assisted screening method includes detecting the molecular marker of N gene or a gene closely linked to N gene in the breeding population material, and screening out an N gene-positive plant for screening a plant comprising the short N introgressed segment according to the result of molecular marker detection.

A method of screening a plant comprising the short N introgressed segment includes using an N introgressed segment-specific molecular marker, or a molecular marker closely linked to the N introgressed segment, or a phenotypic marker closely linked to the N introgressed segment; preferably, a molecular marker of the end of the N introgressed segment; and more preferably, a molecular marker amplified by the TN5.51 primer pair.

A method for detecting a molecular marker includes PCR detection, molecular hybridization, and the like, with the preference of PCR detection. A method for detecting PCR amplification product includes electrophoresis detection. The electrophoretic detection includes agarose gel electrophoresis and detection with fragment analyzer. The method for molecular hybridization comprises hybridizing a nucleic acid sample in screened population material with a partial nucleic acid segment of a molecular marker, amplified by a TN5.51 primer pair, as a probe.

The present invention also discloses a method of breeding a TMV-resistant tobacco comprising a short N introgressed segment. The TMV-resistant tobacco comprising the short N introgressed segment was hybridized with a second tobacco plant having nn genotype, and the TMV-resistant tobacco comprising the short N introgressed segment was selected among the hybridized descendants. A TMV-resistant tobacco line or variety comprising the short N introgressed segment is obtained by a conventional breeding method. The phenotype of the second plant includes, but is not limited to disease resistance and high yield. The hybridization method include self-pollination or hybridization between a pollen donor and a pollen receptor (male fertile or male sterile) to obtain a hybrid or a male sterile hybrid. One or both of the pollen receptor or the pollen donor comprise the short N introgressed segment.

The DNA fragment of the nucleotide sequence set forth in SEQ ID NO. 13 disclosed in the present invention is a chromosome segment of *Nicotiana glutionsa* closely linked to N gene. Transferring the resistance of N gene by hybridization is actually transferring a chromosome segment of *Nicotiana glutionsa* comprising N gene. The sequence set forth in SEQ ID NO. 13 is a partial sequence closely linked to N gene on the N introgressed segment, and specifically, is a non-target genomic component linked to N gene. The genomic component comprising the sequence set forth in SEQ ID NO. 13 bring linkage drag in a common tobacco. Knocking out a partial or entire sequence set forth in SEQ ID NO. 13 reduce the linkage drag. It will be understood by those skilled in the art that when a partial or entire sequence set forth in SEQ ID NO. 13 is knocked out, the effect of the present invention can also be achieved by simultaneous knock out of the upstream and downstream sequences of the 5' end and/or the 3' end of SEQ ID NO. 13. The length of the upstream and downstream sequences of the 5' end and/or the 3' end of SEQ ID NO. 13 is appropriate, and is not particularly limited, for example, more than 1 Kb, more than 10 Kb, more than 50 Kb, more than 100 Kb, more than 500 Kb, more than 1000 Kb, more than 2000 Kb or more than 5000 Kb.

The invention further discloses use of the TMV-resistant tobacco plant comprising the short N introgressed segment in breeding a TMV-resistant tobacco variety as above.

The present invention provides a TMV-resistant tobacco plant comprising a short N introgressed segment. The molecular marker of the present invention is used to reduce the non-target genomic component linked to N gene on the N introgressed segment, rather than to evaluate whether there is any resistance mediated by N gene, compared to N gene resistance-related molecular marker that has been reported. Conventional breeding techniques fail to screen out a chromosome crossover plant comprising short N introgressed segment from the breeding population. In the invention, a breeding population is prepared and screened with N right-end molecular marker TN5.51, N gene-specific molecular marker and SEQ ID NO. 13 molecular marker, to obtain the chromosome crossover plant comprising the short N introgressed segment from a large breeding population material, and to preliminarily identify the number of the reduced non-target genomic components. The TMV-resistant plant comprising the short N introgressed segment obtained in the invention is used for creating a novel TMV-resistant germplasm resource, and breeding the TMV-resistant tobacco variety, which are beneficial to reduce the drag linked to N gene.

DESCRIPTION OF THE FIGURES

FIG. 1 is result of electrophoretic detection for a product of a plant comprising a short N introgressed segment amplified with N1N2, TN4.99, TN5.20, TN5.34, and TN5.51 primer pairs;

In FIG. 1, from left to right, 1st, 6th, 11th, 16th, and 21th lanes are 100 bp DNA Ladder; 2nd to 5th lanes are Coker176, 15-7F, 24-8H, 99-2D, respectively; amplified with the primer pair N1N2; 7th to 10th lanes are Coker176, 15-7F, 24-8H, 99-2D amplified with TN4.99; 12th to 15th lanes are Coker176, 15-7F, 24-8H, 99-2D amplified with the primer pair TN5.20; 17th to 20th lanes are respectively Coker176, 15-7F, 24-8H, 99-2D amplified with the primer pair TN5.34; 22th to 25th lanes are respectively Coker176, 15-7F, 24-8H, 99-2D amplified with the primer pair TN5.51.

DETAILED DESCRIPTION OF THE INVENTION

To illustrate the purposes, technical solutions and advantages of the present invention, the present invention will be further described in detail with reference to the figures and examples. Where specific techniques or conditions are not indicated in the examples, they are carried out according to the techniques or conditions described in the art or in accordance with the product specifications. Where the reagents or instruments used are not specified by the manufacturer, they are conventional products that can be commercially available. Obviously; the described examples are only a part of the examples of the present invention, rather than all of the examples. All other examples obtained by those skilled in the art based on the examples of the present invention without creative work shall be within the scope of the present invention.

A TMV-resistant tobacco plant Coker176 comprising an N introgressed segment and a TMV-susceptible material Yunyan 87 excludes an N introgressed segment are used. The above tobacco plants are common tobacco germplasm resources, which can be obtained by the public from a tobacco germplasm resources depositary authority or the Yunnan Academy of Tobacco Agricultural Sciences.

The DNA extraction kit was purchased from QIAGEN. DNA Marker and Taq DNA polymerase were purchased from Takara Biomedical Technology (Dalian) Co., Ltd. Other chemical reagents are commercially available products. The primers used in the present invention are listed in Table 1.

TABLE 1

Primer sequences

| | | |
|---|---|---|
| GL4.06 | Forward primer | 5'-GATCCCACGAGTGGAGCA-3' (SEQ ID NO. 1) |
| | Reverse primer | 5'-TCCTCACCAAACCCAACTTT-3' (SEQ ID NO. 2) |
| TN5.20 | Forward primer | 5'-CGACTTTCAAAGGGAATCCA-3' (SEQ ID NO. 3) |
| | Reverse primer | 5'-TGCCTGCCAAGTGACTACAG-3' (SEQ ID NO. 4) |
| TN4.99 | Forward primer | 5'-TGCCACACAGGGTGACTAGA-3' (SEQ ID NO. 5) |
| | Reverse primer | 5'-AAGCAAAACTGTGTCATTAGGC-3' (SEQ ID NO. 6) |
| TN5.51 | Forward primer | 5'-TTCGGGTTTTTAGTTCGGTTT-3' (SEQ ID NO. 7) |
| | Reverse primer | 5'-AGGCACCATGTCACAAACA-3' (SEQ ID NO. 8) |
| TN5.34 | Forward primer | 5'-CACTTTGGCCTGTCACACAA-3' (SEQ ID NO. 9) |
| | Reverse primer | 5'-AAACTTGTTCATAGTCTGCGAAT-3' (SEQ ID NO. 10) |
| N1N2 | Forward primer | 5'-CGTCGACACATTATGCCATC-3' (SEQ ID NO. 11) |
| | Reverse primer | 5'-GAGGGGTCTTACCCCATTGT-3' (SEQ ID NO. 12) |

Example 1 Preparation of Plant Materials and DNA Extraction (1) Backcrossing of N Introgressed Segment Coker176 (NN genotype, which is negative for the GL4.06 primer pair and positive for the TN5.51 primer pair) and Yunyan 87 (nn genotype) are planted. Coker176 pollen is collected during flowering and pollinated to the emasculated Yunyan 87 flower, to obtain the F1 seed (Nn genotype). The F1 plant were planted. F1 pollen was collected during flowering and pollinated to the emasculated Yunyan 87 flower to obtain the BC1F1 seed (genotype Nn:nn=1:1). BC was seeded, and TMV was inoculated during the seedling stage, and a TMV-resistant plant (Nn genotype) was screened out. During flowering, the pollen was collected and backcrossed to Yunyan 87, to obtain the backcross seed. By continuous backcrossing, 5 grams of backcrossed 3rd descendant (BC3F1) seeds were obtained. A plant comprising the N introgressed segment as long as that of Coker176 type was screened out from the BC3F1, and named as Y87N.

(2) Screening of TMV-Resistant Plants 4-5 leaves of tobacco seedlings of BC3F1 backcross population were planted in a 32-well plate, 1 plant per well. TMV was artificially inoculated, and the inoculated leaves were detected to determine whether hypersensitive reactions (lesions) appeared in 5-7 days after inoculation. 5000 individual plants with lesions were selected (Nn genotype), and young leaves were collected for DNA extraction and for screening of plants comprising the short N introgressed segment.

(3) DNA Extraction

DNA was extracted with DNase plant 96 Plant Kit (QIAGEN, Catalogue no. 69181) with reference to the reagent instructions.

Example 2 Screening of Plants Comprising a Short N Introgressed Segment

A TMV-susceptible tobacco variety Yunyan 87 was used as a susceptible control. A TMV-resistant tobacco variety Coker176 comprising the N introgressed segment was used as a resistant control. The TN5.51 primer pair was used in the PCR amplification and the amplification product were detected by electrophoresis, in which the genomic DNAs of the tobacco to be detected, of the susceptible control tobacco and the resistant tobacco control, were used as templates.

The PCR reaction system is as follows:

| | |
|---|---|
| DNA template 50 ng/μL | 2.5 μL, |
| 10 × PCR buffer | 2.0 μL, |
| dNTPs 2.5 mM | 1.2 μL, |
| primer pair10 μmol/μL | each 1.5 μL, |
| Ex-Taq DNase 5 U/μL | 0.3 μL, |
| ddH$_2$O | balance, | wherein the total volume was 20 μL.

Those skilled in the art should understand that the expression "primers pair 10 μmol/μL, each 1.5 μL," means the concentration of the forward primer and reverse primer in the primer pair was 10 μmol/μL, and the amount was 1.5 μL. The primer pair was TN5.51 primer pair.

The reagents used were purchased from Takara Bio.

The PCR reaction procedure was as follows: pre-denaturation at 94° C. for 5 minutes; 35 cycles of denaturation at 94° C. for 30 seconds, annealing at 55° C. for 30 seconds, extension at 72° C. for 30 seconds; and finally extension at 72° C. for 10 minutes. The PCR amplification products can be stored at 4° C.

Electrophoresis detection of PCR products: electrophoresis was carried out with 1.2% by mass of agarose gel at 120V for 25 min, EB staining was performed for 10 min, and the gel was captured and recorded. The results are shown in FIG. 1.

PCR amplification as performed according to the reported method with N gene-specific molecular marker N1N2 (Lewis, R S, S R Milla, and J S Levin. Molecular and genetic characterization of *Nicotiana glutinosa* L. chromosome segments in tobacco mosaic virus-resistant tobacco accessions. Crop Sci. 2005, 45: 2355-2362.).

The plant detected as negative for the TIS 5.51 primer pair and positive for the N1N2 marker was screened out from the tobacco plants, and then TN4.99 primer pair and TN5.20 primer pair and TN5.34 primer pair were used to estimate the size of the deleted genomic component of the plant.

The TN5.51 primer pair was used for amplification. The resistant control had 845 bp amplification product, and the susceptible control had no 845 bp amplification product, indicating that the PCR amplification was normal. Then, the chromosome crossover plant comprising the short N introgressed segment was screened according to the following criteria: If the plant was detected as positive for the N1N2 and had no 845 bp amplification product, it was preliminarily determined to be a chromosome crossover plant comprising a short N introgressed segment; if the plant was detected as positive for the N1N2 and had 845 bp amplification product, it did not involve the chromosome crossover of the N introgressed segment. The results shows that 5000 plants exhibiting lesions were screened out from BC3F1 plants of 11,000 Yunyan 87×Coker176 by inoculation of TMV. The leaves of the plants exhibiting the lesions were collected, and DNA was extracted. Three plants, such as 15-7F and 99-2D and 24-8H, were screened as positive for the N1N2 and having no 845 bp amplification product by TN5.51 marker and N1N2 marker detections. These three plants are chromosome crossover plants comprising the short N introgressed segment. Three plants were self-crossed, with the seed thereof being reserved, and back-crossed with Yunyan 87 to obtain seed of 15-7F BC4F1 line and 99-2D BC4F1 line and 24-8H BC4F1 line.

Example 3: Detection of the Reduced Size of the Non-Target Genomic Components Linked to N Gene A TMV-susceptible tobacco variety Yunyan 87 was used as susceptible control. A TMV-resistant tobacco variety Coke 176 comprising N gene was used as a resistant control. PCR amplification was performed, and amplified products were detected by electrophoresis, wherein DNA of 3 plants positive for the N1N2 and without 845 bp amplification products, genomic DNA of the susceptible tobacco control and genomic DNA of the resistant tobacco control were used as templates. The PCR reaction system is as follows:

| | |
|---|---|
| DNA template 50 ng/μL | 2.5 μL, |
| 10 × PCR buffer | 2.0 μL, |
| dNTPs 2.5 mM | 1.2 μL, |
| primers in the primer pair 10 μmol/μL | each 1.5 μL, |
| Ex-Taq DNase 5 U/μL | 0.3 μL, |
| ddH$_2$O | balance, | wherein the total volume was 20 μL.

The primer pair used was TN4.99 primer pair or TN5.20 primer pair or TN5.34 primer pair.

The reagents used were purchased from Takara Bio.

The PCR reaction procedure was as follows: pre-denaturation at 94° C. for 5 minutes; 35 cycles of denaturation at 94° C. for 30 seconds, annealing at 55° C. for 30 seconds, extension at 72° C. for 30 seconds; and finally extension at 72° C. for 10 minutes. The PCR amplification products can be stored at 4° C.

Electrophoresis detection of PCR products: electrophoresis was carried out with 1.2% by mass of agarose gel at 120V for 25 min, EB staining was performed for 10 min, and the gel was captured and recorded. The results are shown in FIG. 1.

TN4.99 primer pair, TN5.20 primer pair, TN5.34 primer pair and N1N2 primer pair were used for amplification, respectively. The resistant control showed amplified products of the tested primer pair, and the susceptible control did not show amplified products of the tested primer pair. This indicates that the PCR amplification is normal. The genomic component of the plant with chromosome crossover comprising the short N introgressed segment is then evaluated according to the following criteria: If it is negative for the TN5.34 primer pair, the genomic component between the genes corresponding to the TN5.34 marker and the TN5.51 marker was deleted from the plant. If it was negative for both the TN5.20 primer pair and the TN5.4 primer pair, the genomic component between the genes corresponding to the TN5.20 marker and the TN5.51 marker was deleted from the plant. If it was negative for the TN4.99, the TN5.20 primer pair and the TN5.4 primer pair, the genomic component between the genes corresponding to the TN4.99 marker and the TN5.51 marker was deleted from the plant.

The results show that the 24-8H plant was detected as negative for the TN4.99 primer pair and the TN5.20 primer pair and the TN5.34 primer pair, and positive for the N1N2 primer pair. The physical distance from the marker amplified by the TN4.99 primer pair to tomato chromosome 11 was 4.99 Mb, and the physical distance from TN5.51 to tomato chromosome 11 was 5.51 Mb. It was estimated that the 24-8H plant was shortened by at least 0.52 Mb (the physical distance of tomato chromosome 11), Since the genomic size of the wild species N. glutinosa is estimated 3 times larger than the tomato genomic size, it was estimated that the N introgressed segment of the 24-8H plant is shortened by at least 1.56 Mb. The results show that the 15-7F plant was detected as negative for the TN5.20 primer pair and the TN5.34 primer pair and positive for the N1N2 primer pair and the TN4.99 primer pair. The physical distance from the marker of the TN5.20 primer pair to tomato chromosome 11 was 5.20 Mb, and the physical distance of the marker of the TN5.51 to tomato chromosome 11 was 5.51 Mb. It was estimated that the 15-7F plant was shortened by at least 0.31 Mb (the physical distance of tomato chromosome 11), Since the genomic size of the wild species is estimated 3 times larger than the tomato genomic size, it was estimated that the N introgressed segment of the 15-7F plant is shortened by at least 0.93 Mb.

The results show that the 99-2D plant was negative for the TN5.34 primer pair and positive for N1N2 primer pair, the TN 4.99 primer pair and the TN5.20 primer pair. The physical distance from the marker amplified by the TN5.34 primer pair to tomato chromosome 11 was 5.34 Mb, and the physical distance from TN5.51 to tomato chromosome 11 was 5.51 Mb. It was estimated that the 99-2D plant was shortened by at least 0.17 Mb (the physical distance of tomato chromosome 11). Since the genomic size of the wild species is estimated 3 times larger than the tomato genomic size, as estimated that the N introgressed segment of the 99-2D plant is shortened by at least 0.51 Mb.

Example 4 Screening of Individual Plant Comprising the Short N Introgressed Segment and Detection of the Reduced Size of the Non-Target Genomic Components in 5FN Segregation Population (1) Backcross Breeding of a Population Comprising N Introgressed Segment Coker176 (NN genotype, which is detected as negative for the GL4.06 primer pair and positive for the TN5.51 primer pair) and 5F (nn genotype) are planted. Coker176 pollen was collected during flowering and pollinated to the emasculated 5F flower, to obtain a F1 seed (Nn genotype). A F1 plant was planted. F1 pollen was collected during flowering and pollinated to the emasculated 5F flower to obtain a BC1F1 seed (genotype Nn:nn=1:1). BC1F1 was seeded. TMV was inoculated during the seedling stage, and TMV resistant plant (Nn genotype) was screened out. During flowering, the pollen was collected and backcrossed to 5F, to obtain the backcross seed. By continuous backcrossing, 5 grams of backcrossed 6th descendant (BC6F1) seeds were Obtained. After backcrossing to 4th generation, one plant comprising N introgressed segment as long as that of a plant of Coker176 type was selected to self-cross to obtain BC4F6 seed, which was named 5FN. The TMV-resistant plant (Nn genotype) was screened out from the 5FxCoker176 BC6F1 population according to the method of Example 1, and the DNA was extracted.

The plant comprising short N introgressed segment was screened out according to the method of Example 2. The results shows that 9984 plants exhibiting lesions were screened out from 20,160 BC6F1 plants of 5FxCoker176 by inoculation of TMV. The leaves of the plants exhibiting lesions were collected and the DNA was extracted. The 1-1002 plant positive for the N1N2 and without 845 bp amplification product was screened out from 9612 copies of DNA by detection with TN5.51 marker and N1N2 marker. The plant is a chromosome crossover plant comprising the short N introgressed segment.

According to the method of Example 3, the reduced size of non-target genomic components linked to N gene in the 1-1002 plant was detected. The results show that 1-1002 plant was detected as negative for the TN4.99 primer pair and the TN5.20 primer pair and the TN5.34 primer pair, and positive for the N1N2 primer pair. The physical distance from the marker amplified by the TN4.99 primer pair to tomato chromosome 11 was 4.99 Mb, and the physical distance from TN5.51 to tomato chromosome 11 was 5.51 Mb. It was estimated that the 1-1002 plant was shortened by at least 0.52 Mb (the physical distance of tomato chromosome 11). Since the genomic size of the wild species is estimated 3 times larger than the genomic size of the tomato, it was estimated that the N introgressed segment of the 1-1002 plant is shortened by at least 1.56 Mb.

The plant was self-crossed, with the seed thereof being reserved, and backcrossed with 5F. The 5Fx1-1002 BC7F1 seed was harvested for the detection of the linkage drag phenotypes of the plant comprising the short N introgressed segment, i.e., detection for the yield of plant comprising the short N introgressed segment and detection of chlorophyll content in the upper leaves during the mature stage.

Example 5 Yield of Plant Comprising the Short N Introgressed Segment and Detection of Chlorophyll Content in the Upper Leaves During the Mature Stage 5Fx1-1002 BC7F1 line (½ of which is plant comprising Ns segment), 5FN BC4F6 line (homozygous N segment) and 5F (nn) were seeded. The N-gene positive plant, that is, the plant comprising Ns segment in the 5Fx1-1002 BC7F1 line, were screened out from the 5Fx1-1002 BC7F1 line by PCR screening with the N1N2 marker before transplanting. The plants were planted in the field, topping on the same day during blooming. 18-21 leaves to be collected and can be cured were maintained for each plant, and the middle of the third leaf counted from top to bottom were sampled. The measurement and sampling were performed every 7 days from the 5th week after topping, and sampling was performed for 4 times. Leaf tissue with a width of about 1 cm on both sides of the leaf midrib was drawn with a blade and collected, wrapped with aluminum foil, frozen in liquid nitrogen, and stored in a refrigerator at −80° C. Chlorophyll a, chlorophyll b, lutein, and β-carotene contents were determined by HPLC. The method of determination was according to the standard of the tobacco industry (Determination of plastid pigments of tobacco and tobacco products by high pressure liquid chromatography according to YC/T 382-2010). The yield was determined by a conventional method. The results show that the yield of 5Fx1-1002 BC7F1 line was increased by 3% and the chlorophyll content of upper leaf during the mature stage was decreased by 3%, compared with that of the TMV-resistant tobacco plant 5FN comprising the untruncated N introgressed segment. The yield of 5Fx1-1002 BC7F1 line was comparable to that of 5F. The yield of 5Fx14002 BC7F1 line was higher than that of 5FN. The chlorophyll content of 5Fx1-1002 BC7F1 line was comparable to that of 5F before the upper leaf was cured. The chlorophyll content of 5Fx14002 BC7F1 was lower than the chlorophyll content of 5FN before the upper leaf was cured. The linkage drag traits of the TMV-resistant 1-1002 plant comprising the short N introgressed segment were significantly improved.

The basic concept, main features, and advantages of the present invention are indicated and described above. It should be understood by those skilled in the art that the present invention is not limited by the foregoing examples. Examples and descriptions above only illustrate the concept of the present invention. Any modification and improvements are intended to be included within the scope of the claimed invention, without departing from the spirit and scope of the invention.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11259473B2). An electronic copy of the "Sequence Listing" will also be available from the USPTO upon request and payment of the fee set forth in 37 CFR 1.19(b)(3).

The invention claimed is:

1. A TMV-resistant tobacco plant comprising a short N introgressed segment, wherein a drag genomic component with the sequence as set forth in SEQ ID No. 13 is deleted or a drag genomic component comprising nucleotides located at positions of 120,988 to 806,914 as set forth in SEQ ID NO: 13 is deleted, compared to an N introgressed segment of Coker 176 type tobacco accessions.

2. The TMV-resistant tobacco plant comprising a short N introgressed segment according to claim 1, wherein the plant is
   a tobacco plant that is detected as positive for N1N2 marker and negative for TN4.99 primer pair, TN5.20 primer pair, TN5.34 primer pair and TN5.51 primer pair.

3. The TMV-resistant tobacco plant comprising a short N introgressed segment according to claim 1, wherein the short N introgressed segment is obtained by means of chromosome crossover, genome editing, chemical mutagenesis or physical mutagenesis.

4. The TMV-resistant tobacco plant comprising a short N introgressed segment according to claim 1, wherein the plant is derived from *Nicotiana* genus.

5. A tobacco hybrid, a variety or a line bred from the TMV-resistant tobacco plant comprising a short N introgressed segment according to claim 1.

6. A seed, a pollen and an ovule of the TMV-resistant tobacco plant comprising a short N introgressed segment according to claim 1.

7. A method for breeding the TMS-resistant tobacco plant comprising a short N introgressed segment-according to claim 1, comprising:
   a) hybridizing a tobacco plant having a homozygous N introgressed segment with a tobacco plant having nn genotype to obtain a F1 tobacco plant having Nn genotype, and then hybridizing the F1 tobacco plant with tobacco plant having nn genotype to obtain a population material for screening the short N introgressed segment;
   b) inoculating TMV to the population material obtained in step a) during the seedling stage, and screening an $N_n$ genotype plan(exhibiting necrotic lesions in the population material; and
   c) genotyping the Nn genotype plant screened in step b) with a molecular marker of TN5.51 primer pair and N gene-specific, molecular marker N1N2 at the right end of the N introgressed segment, and screening for a plant detected as positive for the molecular marker N1N2 and negative for the TN5.51 primer pair,
   thereby obtaining a TMV-resistant tobacco plant comprising a short N introgressed segment according to claim 1.

8. A method for breeding the TMV-resistant tobacco plant comprising a short N introgressed segment according to claim 2, comprising:
   a) hybridizing a tobacco plant having homozygous N introgressed segment with a tobacco plant having nn genotype to obtain a F1 tobacco plant having Nn genotype, and then hybridizing the F1 tobacco plant with a tobacco plant having on genotype to obtain a population material for screening the short N introgressed segment;
   b) inoculating TMV to the population material obtained in step a) during the seedling stage, and screening an Nn genotype plant exhibiting lesions in the population material; and
   c) genotyping the Nn genotype plant screened in step b) with TN4.99 primer pair, TN5.20 primer pair, TN5.34 primer pair, TN5.51 primer pair and N gene-specific molecular marker N1N2, and screening for a plant detected as positive for molecular marker N1N2 and negative for TN4.99 primer pair, TN5.20 primer pair, TN5.34 primer pair and TN5.51 primer pair,
   thereby obtaining a TMV-resistant tobacco plant comprising a short N introgressed segment according to claim 2.

* * * * *

UNITED STATES PATENT AND TRADEMARK OFFICE
CERTIFICATE OF CORRECTION

| | | |
|---|---|---|
| PATENT NO. | : 11,259,473 B2 | Page 1 of 1 |
| APPLICATION NO. | : 16/648284 | |
| DATED | : March 1, 2022 | |
| INVENTOR(S) | : Yong Liu et al. | |

It is certified that error appears in the above-identified patent and that said Letters Patent is hereby corrected as shown below:

On the Title Page

(87) PCT Pub. No.: "WO2019/056206" should read --WO2019/056205--

Signed and Sealed this
Thirty-first Day of May, 2022

*Katherine Kelly Vidal*

Katherine Kelly Vidal
*Director of the United States Patent and Trademark Office*